United States Patent
Zhang et al.

(10) Patent No.: US 10,267,752 B2
(45) Date of Patent: Apr. 23, 2019

(54) X-RAY PHASE-CONTRAST IMAGING SYSTEM AND IMAGING METHOD

(71) Applicants: Tsinghua University, Beijing (CN); Nuctech Company Limited, Beijing (CN)

(72) Inventors: Li Zhang, Beijing (CN); Zhiqiang Chen, Beijing (CN); Xiaolei Jiang, Beijing (CN); Xiaohua Zhu, Beijing (CN); Xin Jin, Beijing (CN)

(73) Assignees: Tsinghua University, Beijing (CN); Nuctech Company Limited, Beijing (CN)

(*) Notice: Subject to any disclaimer, the term of this patent is extended or adjusted under 35 U.S.C. 154(b) by 105 days.

(21) Appl. No.: 15/328,437

(22) PCT Filed: Nov. 2, 2015

(86) PCT No.: PCT/CN2015/093605
§ 371 (c)(1),
(2) Date: Jan. 23, 2017

(87) PCT Pub. No.: WO2016/070771
PCT Pub. Date: May 12, 2016

(65) Prior Publication Data
US 2017/0227476 A1 Aug. 10, 2017

(30) Foreign Application Priority Data
Nov. 4, 2014 (CN) .......................... 2014 1 0610466

(51) Int. Cl.
*G01N 23/04* (2018.01)
*G01N 23/046* (2018.01)

(52) U.S. Cl.
CPC ........... *G01N 23/046* (2013.01); *G01N 23/04* (2013.01); *G01N 2223/3306* (2013.01);
(Continued)

(58) Field of Classification Search
CPC .... G01N 23/04; G01N 23/046; G01N 23/041; G01N 2223/408; G01N 2223/3306; G01N 2223/401; A61B 6/4035; A61B 6/484
(Continued)

(56) References Cited

U.S. PATENT DOCUMENTS

| | | |
|---|---|---|
| 2011/0293064 A1 | 12/2011 | Huang et al. |
| 2013/0094625 A1 | 4/2013 | Huang et al. |

(Continued)

FOREIGN PATENT DOCUMENTS

| | | |
|---|---|---|
| CN | 101257851 A | 9/2008 |
| CN | 201191275 Y | 2/2009 |

(Continued)

OTHER PUBLICATIONS

Extended European Search Report received in related EP Application No. 15839133.4, dated May 24, 2017; 9 pages.
(Continued)

*Primary Examiner* — Jurie Yun
(74) *Attorney, Agent, or Firm* — Knobbe Martens Olson & Bear LLP

(57) ABSTRACT

The present disclosure relates to X-ray imaging systems and methods. An exemplary system may comprise a distributed X-ray source arrangement, a fixed grating module, an X-ray detecting device, and a computer workstation. In one illustrative implementation, X-ray sources of the distributed incoherent X-ray source arrangement may sequentially generate and emit X-rays to an object to be detected. Further, for each exposure, the X-ray detecting device may receive the X-rays, wherein after a series of stepping exposures and corresponding data acquisitions, at each pixel of the X-ray detecting device, X-ray intensities are represented as an intensity curve; the intensity curve may be compared to an intensity curve in the absence of the object to be detected,
(Continued)

and a pixel value at each pixel may be obtained from a variation of the intensity curves; and image information of the object to be detected may be obtained according to such pixel values.

20 Claims, 5 Drawing Sheets

(52) U.S. Cl.
CPC . *G01N 2223/401* (2013.01); *G01N 2223/408* (2013.01); *G21K 2207/005* (2013.01)

(58) Field of Classification Search
USPC .......................................... 378/6, 36, 62, 87
See application file for complete search history.

(56) References Cited

U.S. PATENT DOCUMENTS

| | | |
|---|---|---|
| 2014/0037059 A1 | 2/2014 | Suft |
| 2014/0185739 A1 | 7/2014 | Tang et al. |

FOREIGN PATENT DOCUMENTS

| | | |
|---|---|---|
| CN | 101532969 A | 9/2009 |
| CN | 101576515 A | 11/2009 |
| CN | 101726503 A | 6/2010 |
| CN | 101943668 A | 1/2011 |
| CN | 101257851 B | 6/2011 |
| CN | 102221565 A | 10/2011 |
| CN | 101576515 A | 7/2012 |
| CN | 102221565 B | 6/2013 |
| CN | 103575750 A | 2/2014 |
| CN | 103903941 A | 7/2014 |
| CN | 105606633 A | 5/2016 |
| EP | 1731099 A1 | 12/2006 |
| EP | 3048441 A | 7/2016 |
| WO | WO 2010/150136 | 12/2010 |
| WO | WO 2011/119629 | 9/2011 |

OTHER PUBLICATIONS

International Search Report and Written Opinion in related PCT Application No. PCT/CN2015/093605 (WO2016/070771), dated Feb. 1, 2016 (12 pgs), and English-language translation of ISR (2 pgs); 14 pages total.

Office Action and Search Report received in related CN Application No. CN201410610466.3 dated Nov. 13, 2017, 7 pages, and concise English language summary thereof, 2 pages; 9 pages.

Extended European Search Report received in related PCT Application No. PCT/CN2015/093605 (WO2016/070771), dated May 24, 2017; 9 pages.

H. Miao et al. "Motionless Phase Stepping in X-Ray Phase Contrast Imaging with a Compact Source", Proceedings of the National Academy of Sciences, vol. 110, No. 48, dated Nov. 26, 2013 (5 pgs), including front correction page issued Dec. 30, 2014 (1 pgs); 6 pages total.

X-RAY PHASE-CONTRAST IMAGING SYSTEM AND IMAGING METHOD

CROSS-REFERENCE TO RELATED APPLICATIONS

This application is U.S. 371 National Phase of and claims priority to PCT Application No. PCT/CN2015/093605, filed on Nov. 2, 2015, published as WO2016/070771, entitled "X-RAY PHASE-CONTRAST IMAGING SYSTEM AND IMAGING METHOD", and which claim benefit/priority to Chinese Patent Application No. 201410610466.3, filed on Nov. 4, 2014, published as CN105606633A, which are incorporated herein by reference in their entirety.

TECHNICAL FIELD

The present disclosure generally relates to an X-ray grating-based imaging technique, and more particularly, to an X-ray phase-contrast imaging system and imaging method.

BACKGROUND

In modern society, X-ray has been widely used, for example in CT scanning apparatus, for scanning and imaging many objects. Generally, conventional X-ray scanning and imaging technique uses X-ray attenuation through materials to nondestructively detect interiors of objects. The more different in density of internal components of the object are, the greater will be the effect of the conventional X-ray imaging technique. Substances consisting of light elements have weak absorbing abilities for X-ray, thus conventional X-ray imaging technique can hardly identify their internal structures. In this case, other auxiliary means, such as injecting contrast agent into biological tissues, do not help to obtain clear images, without which a lot of inconveniences may be caused. In the 1990s, there appeared an X-ray phase-contrast imaging technique which uses information concerning the phase shift of an X-ray beam to observe changes in density of electrons in an object, thereby determining the inner structure of the object. Generally, the early phase-contrast imaging methods use interference or diffraction of coherent or partially coherent X-rays to improve the low-contrast resolution of the radiation image. On such a basis, in the patent applications CN101532969A entitled "System and method for X-ray grating-based phase-contrast imaging" (Patent Reference 1) and CN101726503A entitled "X-ray phase contrast tomography imaging" (Patent Reference 2), wherein all the contents of said patent applications are incorporated into the present application by reference, HUANG Zhifeng et al. put forward a novel technical concept for incoherent grating-based phase-contrast imaging. Specifically, the said references use two absorption gratings which can translate relative to each other for several steps within a range of one grating period, and a detecting device acquires one image for each translation step; after the image acquisition process for one grating period has been finished, for each pixel, the sample intensity curve and the background intensity curve are compared such that the information concerning the refraction image of the object to be detected can be calculated. This approach has a good phase-contrast imaging effect. Said approach can be performed with multicolored and incoherent X-ray sources and thus can be embodied as simple and easy devices.

Furthermore, during the progress of the X-ray imaging technology, there also appeared a dark-field imaging technique. Said dark-field imaging technique uses indirect light such as scattered light, diffracted light, refracted light, fluorescent light and the like to illuminate objects, and then form images of the internal structures of the objects by means of the difference in their capabilities of scattering X-rays. Generally, the dark-field imaging with hard X-rays is difficult to well perform, since the special optical properties of hard X-rays make it is difficult to manufacture optical components required for dark-field imaging with hard X-rays. However, the dark-field imaging with hard X-rays has a better capability to identify and detect the internal microstructures of objects than the bright-field imaging and the phase-contrast imaging. Since the scattering of the hard X-rays is at a micrometer level or a nanometer level, the dark-field imaging with hard X-rays can be used to identify the internal ultrafine structures of objects, which, in contrast, cannot be determined by the bright-field imaging and phase-contrast imaging with hard X-rays. In 2009, in the patent application CN101943668A entitled "X-ray dark-field imaging system and method" (Patent Reference 3), wherein all the contents of said patent application are incorporated into the present application by reference, HUANG Zhifeng et al. put forward a technical solution that performs dark-field imaging of objects by using X-rays. Specifically, the technical solution of the said reference comprises: emitting X-rays to an object to be detected; enabling one of two absorption gratings to perform stepping within at least one period; for each step, the detecting device receiving and converting X-rays into an electrical signal; after stepping over at least one period, representing the X-ray intensity at each pixel of the detecting device as an intensity curve; comparing, at each pixel of the detecting device, the intensity curve with the object to be detected and the intensity curve without the object, and calculating the second moment of the scattering angle distribution at each pixel; taking images of the object from different angles, and then obtaining a scattering information image of the object according to a CT reconstruction algorithm.

The above-mentioned grating-based imaging techniques require the stepping process to obtain the intensity curve at each detection unit (pixel) of the detecting device. The basic principle of the stepping technique is: after a source grating is fixed adjacent to an X-ray source, in the technique based on a Talbot-Lau interference method, a phase grating or resolution grating is relatively translated for several steps within a range of one grating period; while in the technique based on a classic optical method, two absorption gratings are translated relative to each other for several steps in a range of one grating period. The detecting device acquires one image for each translation step. After finishing the image acquisition process for one grating period, for each pixel, the sample intensity curve and the background intensity curve are compared such that the refraction image information, attenuation image information and dark-field image information can be calculated. Generally, conventional stepping technique comprises translating the phase gratings, the resolution gratings or the absorption gratings. In 2010, in the patent application CN102221565A entitled "X-ray source grating-stepping imaging system and imaging method" (Patent Reference 4), wherein all the contents of said patent application are incorporated into the present application by reference, HUANG Zhifeng et al. put forward a grating stepping method for an X-ray source. Specifically, since the source grating has a period of dozens of micrometers, the above approach requires a substantially lower stepping accuracy as compared to the conventional stepping methods.

Nevertheless, the stepping technique adversely affects application of grating-based imaging technique when they are used in combination. A stepping process by means of mechanical systems will be time-consuming and thus increase scanning time. Moreover, even for a stepping action of about a few tens of micrometers, high equipment accuracy, good shock absorption and an appropriate environment temperature will be required. Both of the above factors impede the application of those new grating-based imaging techniques.

SUMMARY

On the basis of existing techniques such as X-ray grating-based phase-contrast imaging, dark-field imaging and X-ray source-grating-stepping imaging system, the present disclosure provides an X-ray phase-contrast imaging system and imaging method based on an distributed X-ray source arrangement and achieved in an incoherent manner, which adopts a distributed incoherent X-ray source arrangement instead of conventional X-ray sources, wherein the stepping procedure is replace with a process in which a number of X-ray sources sequentially generate X-rays. Therefore, the imaging system according to the present disclosure can reduce imaging time and does not require high equipment accuracy.

According to an aspect of the present disclosure, there is provided an X-ray imaging system for performing X-ray imaging of objects, comprising:

a distributed X-ray source arrangement, a fixed grating module and an X-ray detecting device that are sequentially arranged in an X-ray propagation direction, wherein during an X-ray imaging process, an object to be detected is disposed between the distributed X-ray source arrangement and the fixed grating module;

the fixed grating module comprises a first grating and a second grating which are disposed in the X-ray propagation direction in parallel to each other and are fixed relative to each other;

X-ray sources of the distributed X-ray source arrangement are arranged in a direction perpendicular to both the X-ray propagation direction and a grating strip direction;

the X-ray phase-contrast imaging system further comprises a computer workstation, which is configured to control the distributed X-ray source arrangement and the X-ray detecting device such that:

the X-ray sources of the distributed X-ray source arrangement sequentially generate X-rays to emit X-rays to the object to be detected;

for each exposure, the X-ray detecting device receives the X-rays, wherein after a series of stepping exposures of the distributed X-ray source arrangement and corresponding data acquisitions, at each pixel of the X-ray detecting device, X-ray intensities are represented as an intensity curve;

the intensity curve at each pixel spot on the X-ray detecting device is compared to an intensity curve in the absence of the object to be detected, and a pixel value at each pixel is obtained from a variation of the intensity curves; and an image of the object to be detected is reconstructed from the obtained pixel values.

The present disclosure gives full play to superiorities of grating-based imaging technique. For example, three kinds of information (i.e., attenuation, phase-contrast and dark-field) that indicate internal structure of object may be simultaneously obtained during one scanning process such that internal structural information and composition information of object can be more fully revealed. Furthermore, the present disclosure adopts a distributed X-ray source arrangement that can generate plural exposures with short intervals and adopts stepping exposure procedure instead of mechanical stepping procedure. Therefore, the present disclosure can perform quick and stable imaging via grating-based imaging technique, and thus can be widely used in various fields such as medical imaging, security checking and the like.

Furthermore, the X-ray imaging system according to the embodiment of the present disclosure further comprises: an actuation device for, under the control of computer workstation, enabling the object to be detected to rotate by an angle relative to other parts of the X-ray imaging system.

Furthermore, in the X-ray imaging system according to the embodiment of the present disclosure, at each rotation angle, the phase stepping and exposure actions are repeated, and then an image of the object to be detected is reconstructed according to a predetermined CT image reconstruction algorithm.

Furthermore, in the X-ray imaging system according to the embodiment of the present disclosure, the distributed X-ray source arrangement is a distributed incoherent X-ray source arrangement.

Furthermore, in the X-ray imaging system according to the embodiment of the present disclosure, the distributed incoherent X-ray source arrangement uses carbon nanotubes as its electron sources.

Furthermore, in the X-ray imaging system according to the embodiment of the present disclosure, the computer workstation comprises: a data processing module, for processing data information and calculating pixel values at respective spots on the object to be detected; an image reconstruction module, for reconstructing an image of the object to be detected based on the calculated pixel values; and a control module, for controlling the distributed X-ray source arrangement and the X-ray detecting device.

Furthermore, in the X-ray imaging system according to the embodiment of the present disclosure, the computer workstation comprises: a display unit for displaying the image of the object to be detected.

Furthermore, in the X-ray imaging system according to the embodiment of the present disclosure, the computer workstation is able to calculate refraction information of X-rays at a predetermined spot on the object to be detected by comparing an intensity curve with the presence of the object to be detected to a background intensity curve in the absence of the object to be detected, and thus calculate corresponding pixel value.

Furthermore, in the X-ray imaging system according to the embodiment of the present disclosure, the computer workstation is able to calculate scattering information of X-rays at a predetermined spot on the object to be detected by comparing an intensity curve with the presence of the object to be detected to a background intensity curve in the absence of the object to be detected, and thus calculate corresponding pixel value.

Furthermore, in the X-ray imaging system according to the embodiment of the present disclosure, the computer workstation is able to calculate attenuation information of X-rays at a predetermined spot on the object to be detected by comparing an intensity curve with the presence of the object to be detected to a background intensity curve in the absence of the object to be detected, and thus calculate corresponding pixel value.

Furthermore, according to an aspect of the present disclosure, there is provided an X-ray imaging method, which performs X-ray imaging of an object by using an X-ray imaging system, wherein the X-ray imaging system comprises: a distributed X-ray source arrangement, a fixed grating module, an X-ray detecting device and a computer workstation, the X-ray imaging method comprising the following steps:

sequentially generating, by X-ray sources of the distributed X-ray source arrangement, X-rays to emit X-rays to an object to be detected;

for each exposure, receiving the X-rays by the X-ray detecting device, wherein after a series of stepping exposures of the distributed X-ray source arrangement and corresponding data acquisitions, at each pixel of the X-ray detecting device, X-ray intensities are represented as an intensity curve;

comparing the intensity curve at each pixel spot on the X-ray detecting device to an intensity curve in the absence of the object to be detected, and obtaining a pixel value at each pixel from a variation of the intensity curves; and reconstructing an image of the object to be detected according to the obtained pixel values.

Furthermore, according to an aspect of the present disclosure, there is provided an X-ray imaging method, comprising the following steps:

sequentially generating, by X-ray sources of a distributed incoherent X-ray source arrangement, X-rays to emit X-rays to an object to be detected;

each time the distributed incoherent X-ray source arrangement emits X-rays, forming an X-ray signal with varying intensities from the X-rays, which are refracted by the object to be detected and then pass through a first absorption grating and a second absorption grating;

by an X-ray detecting device, receiving the X-ray signal with varying intensities and converting the received X-ray signal into an electrical signal;

acquiring, from the converted electrical signal in a multi-period sampling manner, refraction angle information when the X-rays passed through the object, and obtaining pixel values of the object according a predetermined algorithm; and reconstructing an image of the object to be detected from the obtained pixel values.

Furthermore, in the X-ray imaging method according to the embodiment of the present disclosure, the object to be detected is rotated, wherein at each rotation angle, the phase stepping and exposure actions are repeated, and an image of the object to be detected is reconstructed according to a predetermined CT image reconstruction algorithm.

Furthermore, in the X-ray imaging method according to the embodiment of the present disclosure, refraction information of X-rays at a predetermined spot on the object to be detected is calculated by comparing an intensity curve with the presence of the object to be detected to a background intensity curve in the absence of the object to be detected, and thus corresponding pixel value is calculated.

Furthermore, in the X-ray imaging method according to the embodiment of the present disclosure, scattering information of X-rays at a predetermined spot on the object to be detected is calculated by comparing an intensity curve with the presence of the object to be detected to a background intensity curve in the absence of the object to be detected, and thus corresponding pixel value is calculated.

Furthermore, in the X-ray imaging method according to the embodiment of the present disclosure, attenuation information of X-rays at a predetermined spot on the object to be detected is calculated by comparing an intensity curve with the presence of the object to be detected to a background intensity curve in the absence of the object to be detected, and thus corresponding pixel value is calculated.

The present disclosure adopts a distributed incoherent X-ray source arrangement instead of conventional X-ray sources, wherein a conventional stepping procedure which translates gratings via mechanical devices is replace with a process in which a number of distributed X-ray sources sequentially generate X-rays (stepping exposure procedure). Therefore, the imaging system according to the present disclosure can reduce scanning time and does not require high accuracy translation. The imaging system according to the present disclosure does not have high standards with respect to vibration reduction and environment temperature, and thus can facilitate application of grating-based imaging systems.

BRIEF DESCRIPTION OF THE DRAWINGS

FIGS. 3A-3B show a multi-period phase stepping process according to the disclosure, wherein FIG. 3A is a schematic diagram showing an acquisition over plural periods and a multi-period sampling (i.e., its sampling points), and FIG. 3B is a schematic diagram showing a displacement curve for a multi-period sampling.

DETAILED DESCRIPTION

Below, the present disclosure will be described in details by reference to the appended drawings.

Figure 1:
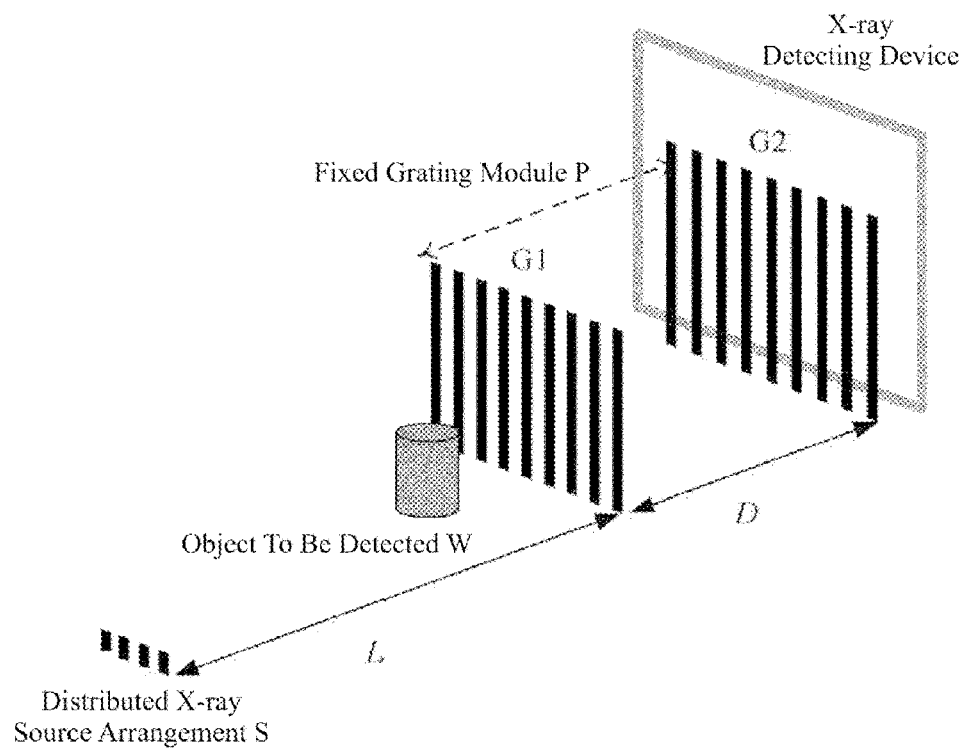
FIG. 1 is a schematic diagram of an X-ray phase-contrast imaging system based on a distributed incoherent X-ray source arrangement according to an embodiment of the disclosure.

FIG. 1 is a schematic diagram of an X-ray phase-contrast imaging system based on a distributed incoherent X-ray source arrangement according to an embodiment of the disclosure. As shown in FIG. 1, an X-ray phase-contrast imaging system according to an exemplary embodiment of the disclosure comprises: a distributed X-ray source arrangement S (in the present disclosure, the distributed X-ray source arrangement S is a distributed incoherent X-ray source arrangement), a fixed grating module P and an X-ray detecting device. Moreover, the distributed X-ray source arrangement S, the fixed grating module P and the X-ray detecting device are sequentially arranged in an X-ray propagation direction. Furthermore, during an imaging process of an object to be detected, the object to be detected W (i.e., an object to be scanned as shown in FIG. 1) is disposed between the distributed X-ray source arrangement S and the fixed grating module P. Moreover, as shown in FIG. 1, multiple X-ray sources (i.e., multiple X-ray focal spots) of the distributed X-ray source arrangement are disposed along a direction perpendicular to both a path of X-ray beam (i.e., the X-ray propagation direction) and a grating strip direction. These X-ray focal spots can emit X-rays in a predetermined sequence. For example, these X-ray focal spots may sequentially emit X-rays. Accordingly, this process can produce an equivalent result to conventional phase stepping procedure.

Furthermore, the distributed X-ray source arrangement according to the present disclosure can utilize for example the distributed X-ray device disclosed in the Chinese Patent Application CN103903941A. The distributed X-ray device can be controlled to emit X-rays from its multiple focal spots (i.e., target spots) in a predetermined sequence. Furthermore, according to one embodiment, the distributed incoherent X-ray source arrangement can utilize carbon nanotubes as its electron sources.

Furthermore, according to the present disclosure, the fixed grating module P comprises two high-accuracy gratings G1 and G2. The two gratings G1 and G2 are parallel to each other. In the grating-based imaging process according to the above-mentioned references, two high-accuracy gratings perform phase stepping actions to achieve the phase stepping process. According to the present disclosure, the gratings G1 and G2 are fixed relative to each other and have a distance D therebetween. There may be a distance L between the distributed X-ray source arrangement S and the grating G1. Furthermore, the two gratings G1 and G2 have periods $p_1$ and $p_2$ respectively, and are sequentially arranged in the X-ray propagation direction in parallel to each other.

Furthermore, the periods of the gratings G1 and G2 are preferably between 0.1 and 30 μm. The absorbing material of the gratings is heavy metal (such as gold (Au)). For example, the height of the gold absorbing material is determined by the applied X-ray energy, and is generally between 10 and 100 μm. For example, for X-rays of 20 keV, gold with a height of more than 16 μm can block 90% of the X-rays.

Furthermore, the X-ray detecting device is adapted to receive X-rays and transform the received X-rays into digitally processable electrical signals via photoelectric conversion (for example, digital radiography). Preferably, the X-ray detecting device can be an array detecting device, wherein each detecting unit (pixel) can detect intensity variation of X-rays impinged on the detecting unit. Preferably, the X-ray detecting device can regularly perform collecting and transforming of X-rays. Preferably, a medical detecting device having a planar array arrangement and low noise can be utilized. A planar array detecting device with a dynamic range larger than 12 bit can cover the whole imaging area. In order to detect calcified breast tissues of hundreds of micrometers, the X-ray detecting device will have a spatial resolution of or less than hundreds of micrometers, for example between 70 and 100 μm.

Furthermore, the X-ray phase-contrast imaging system according to the present disclosure further comprises a computer workstation. All of the control of the entire imaging system, data transmission, image reconstruction and data processing can be accomplished by the computer workstation. The scanning control information, position information, projection data and the like are input into the computer workstation via a data acquisition system. The computer workstation performs extraction of many kinds of information of the object, data preprocessing and image reconstruction, and then displays them on a display.

Furthermore, the computer workstation may comprise a data processing module. The data processing module is configured to: calculate variation in the intensity (curve) after the X-ray passes through the object to be detected according to digitally processable electrical signals output from the X-ray detecting device; calculate the absorption information, scattering information or refraction information at a certain point on the object to be detected with respect to the X-ray according to the variation in said intensity (curve); and calculate the pixel information concerning the object to be detected by use of the aforementioned information. These functions can also be achieved by programmed software, or alternatively achieved by a dedicated hardware chipset.

Furthermore, the computer workstation may further comprise a control module (not shown in FIG. 1) for controlling the operations (such as relative rotation, X-ray emission and information acquisition) of the distributed X-ray source arrangement S, the object to be detected W, the fixed grating module P, the X-ray detecting device and the like. Preferably, the control module and the data processing module can be integrated together and implemented by a single general or dedicated processor.

Furthermore, the computer workstation may further comprise an imaging module (not shown in FIG. 1) for reconstructing an image of the object to be detected according to the obtained pixel information, outputting and displaying the image. Moreover, the imaging module may be implemented by the processor that also serves as the data processing module.

Furthermore, the X-ray phase-contrast imaging system according to the disclosure may further comprise an actuation device for enabling the object to be detected to rotate by an angle relative to other parts of the X-ray phase-contrast imaging system under the control of the computer workstation. The phase stepping and exposure process of the distributed X-ray source arrangement is repeated at each rotation angle, and thus pixel values for X-ray imaging may be obtained at multiple angles. Then, a stereo image of the object to be detected is reconstructed according to a predetermined CT image reconstruction algorithm. The actuation device has a structure for achieving a relative rotating of the object to be detected.

Furthermore, the computer workstation may comprise a display unit for displaying the reconstructed image. The display unit can be implemented by a general display.

Figure 2:
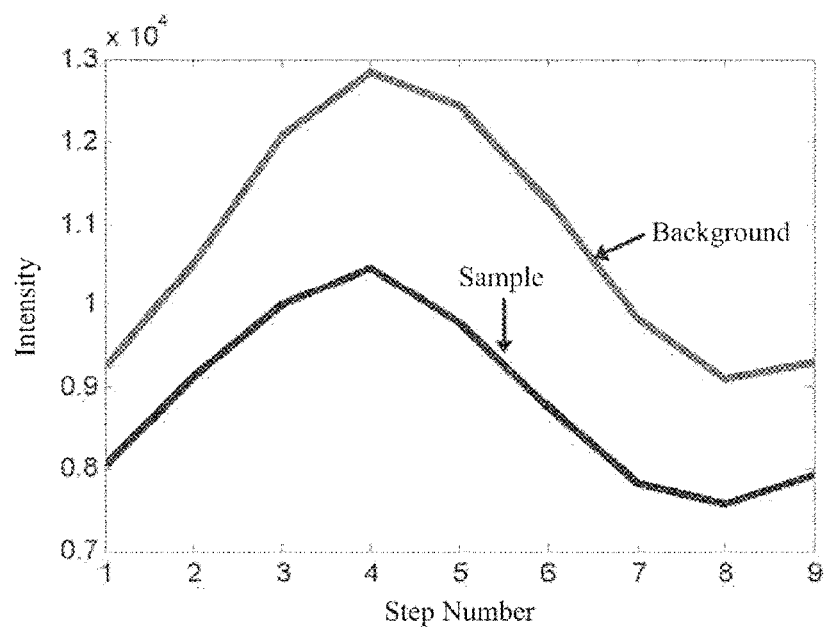
FIG. 2 is a schematic diagram of an intensity curve obtained in a stepping scan process according to an embodiment of the disclosure.

Specifically, an operation process of the X-ray phase-contrast imaging system based on the distributed incoherent X-ray source arrangement according to an embodiment of the disclosure will be described below. For example, according to the present disclosure, the computer workstation controls the distributed X-ray source arrangement S and the X-ray detecting device to perform the following process. The X-ray sources (i.e., X-ray focal spots) of the distributed X-ray source arrangement S sequentially generate X-rays (i.e., a stepping exposure procedure). For each exposure, the X-ray source arrangement S emits X-rays to the object to be detected W, and the X-ray detecting device receives the X-rays. After a series of stepping exposures of the distributed X-ray source arrangement S (i.e., all the X-ray focal spots have sequentially emitted X-rays once) and corresponding data acquisitions, at each pixel of the X-ray detecting device, the intensities of X-rays may be represented as an intensity curve (as shown in FIG. 2). The intensity curve at each pixel spot on the X-ray detecting device is compared to an intensity curve (i.e., background intensity curve) in the absence of the object to be detected W (the intensity curve in the absence of the object to be detected W is known, and can be stored in the computer workstation or input from outside). The pixel value at each pixel spot is calculated from a variation of the intensity curves. Image information of the object to be detected is obtained according to the calculated pixel values. The present disclosure employs the X-ray focal spots of the distributed incoherent X-ray source arrangement to sequentially emit X-rays, instead of performing stepping procedure of two gratings as in prior arts. The present disclosure may use the same method with the prior art to perform data acquisition, obtaining and comparing of intensity curves, calculation of pixel values, reconstruction of images and the like.

Figure 3A:
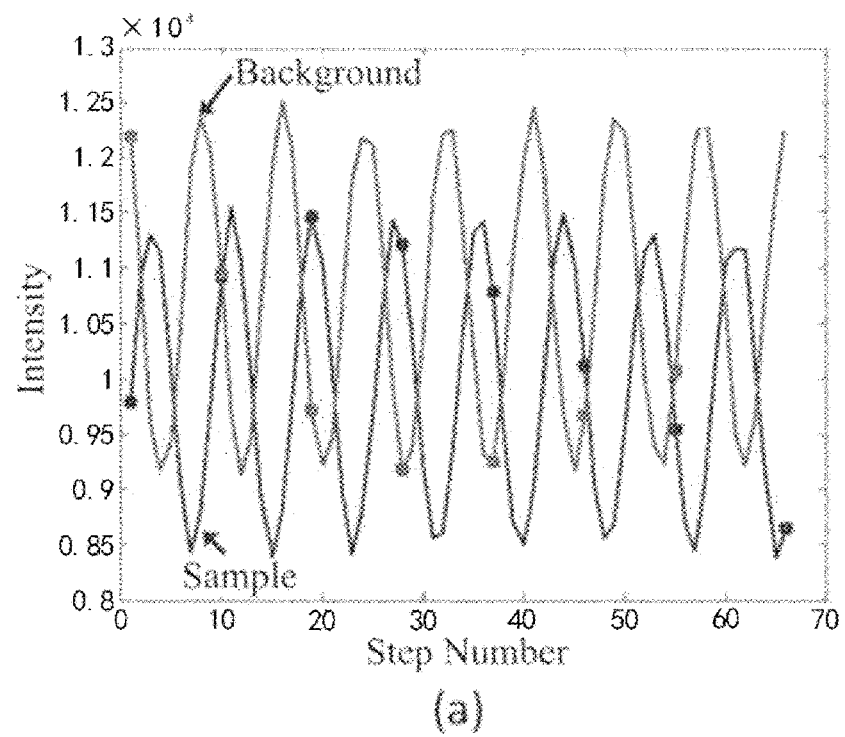
Figure 3B:
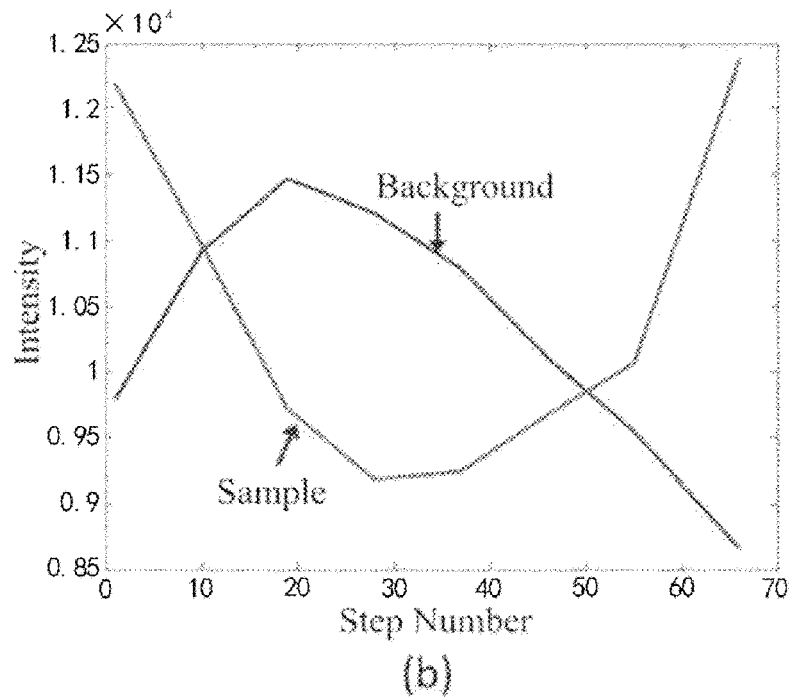

Especially, the phase stepping and exposure process of the distributed X-ray source arrangement according to the present disclosure is developed in view of the X-ray source grating-stepping imaging approach of the above Patent Reference 4. In the conventional phase stepping procedure, one of gratings is moved within one grating period. However, it will be difficult to directly apply the approach of the above Patent Reference 4 to perform the phase stepping and exposure process of the distributed X-ray source arrangement according to the present disclosure, since some of the X-ray sources of the distributed X-ray source arrangement will overlap with each other otherwise. Therefore, the present disclosure provides a multi-period phase stepping procedure, and on this basis provides an X-ray phase-contrast imaging system and imaging method based on a distributed incoherent X-ray source arrangement. FIG. 3 shows diagrams of sampling and displacement curves. FIG. 3 shows a multi-period phase stepping process, wherein part (a) of FIG. 3 is a schematic diagram showing an acquisition over plural periods and a multi-period sampling (i.e., its sampling points), and part (b) of FIG. 3 is a schematic diagram showing a displacement curve for a multi-period sampling. Specifically, a conventional phase stepping process is finished within one period, which corresponds to the sinusoidal curve shown in part (a) of FIG. 3. The present disclosure provides a multi-period phase stepping procedure which is finished over plural grating periods (i.e., sampling over plural periods). For example, a conventional phase stepping process may comprise N sampling points (i.e., N steps). Correspondingly, the multi-period phase stepping process according to the disclosure should be performed over N periods, with one sample obtained during each period. For example, in the first period, a sample is obtained at a point corresponding to the first sampling point according to the conventional phase stepping process; in the second period, a sample is obtained at a point corresponding to the second sampling point according to the conventional phase stepping process; in the third period, a sample is obtained at a point corresponding to the third sampling point according to the conventional phase stepping process; . . . ; in the N-th period, a sample is obtained at a point corresponding to the N-th sampling point according to the conventional phase stepping process. Due to periodicity of sinusoidal curve, the sampling process according to the disclosure can have the same effect with the conventional phase stepping process. The sampling process according to the disclosure can advantageously provide a possibility of placement of the distributed X-ray source arrangement and thus can provide a basis for the employed imaging method. Otherwise, if the disclosure employs the conventional phase stepping process, the distributed X-ray source arrangement cannot be disposed appropriately.

As described above, the disclosure combines the distributed incoherent source arrangement and the multi-period sampling procedure. However, the disclosure is not limited to this. The multi-period sampling procedure according to the disclosure can also be applied in existing X-ray phase-contrast imaging system.

According to the above analysis, the requirements of the distributed X-ray source arrangement will be described below. The distributed X-ray source arrangement according to the disclosure is a distributed incoherent X-ray source arrangement.

I. Requirement for Size of Single X-Ray Source

The period of the source grating $G_0$ defined in the cited Patent Reference 1 will be used: $p_0=(p_1 p_2)/(p_2-p_1)\Box(l/p_1)\lambda$, wherein $p_0$, $p_1$ and $p_2$ denotes the periods of the three gratings $G_0$, $G_1$ and $G_2$ respectively, l is a distance from the grating $G_0$ to the grating $G_1$, and $\lambda$ is a wavelength of X-ray. Therefore, in the disclosure, each X-ray source of the distributed X-ray source arrangement has a focal spot size not greater than $D=p_0 \cdot DC$ wherein DC denotes a duty cycle of the source grating and is defined as a ratio between an opening size and the grating period.

II. Requirement for Intervals Between X-Ray Sources of the Distributed X-Ray Source Arrangement According to the aforementioned multi-period phase stepping process, for a distributed X-ray source arrangement comprising "n" (number n) focal spots, an interval between neighboring focal spots is defined as: $d=(m+1/n) \cdot p_0$, $m=1, 2, 3, \ldots$, wherein m is an arbitrary integer. A larger value of "m" can increase intervals between neighboring X-ray source and reduce processing difficulty.

As described above, the disclosure combines the distributed incoherent X-ray source arrangement and the multi-period sampling procedure. However, the disclosure is not limited to this. The multi-period sampling procedure according to the disclosure can also be applied in other X-ray phase-contrast imaging systems.

Figure 4:
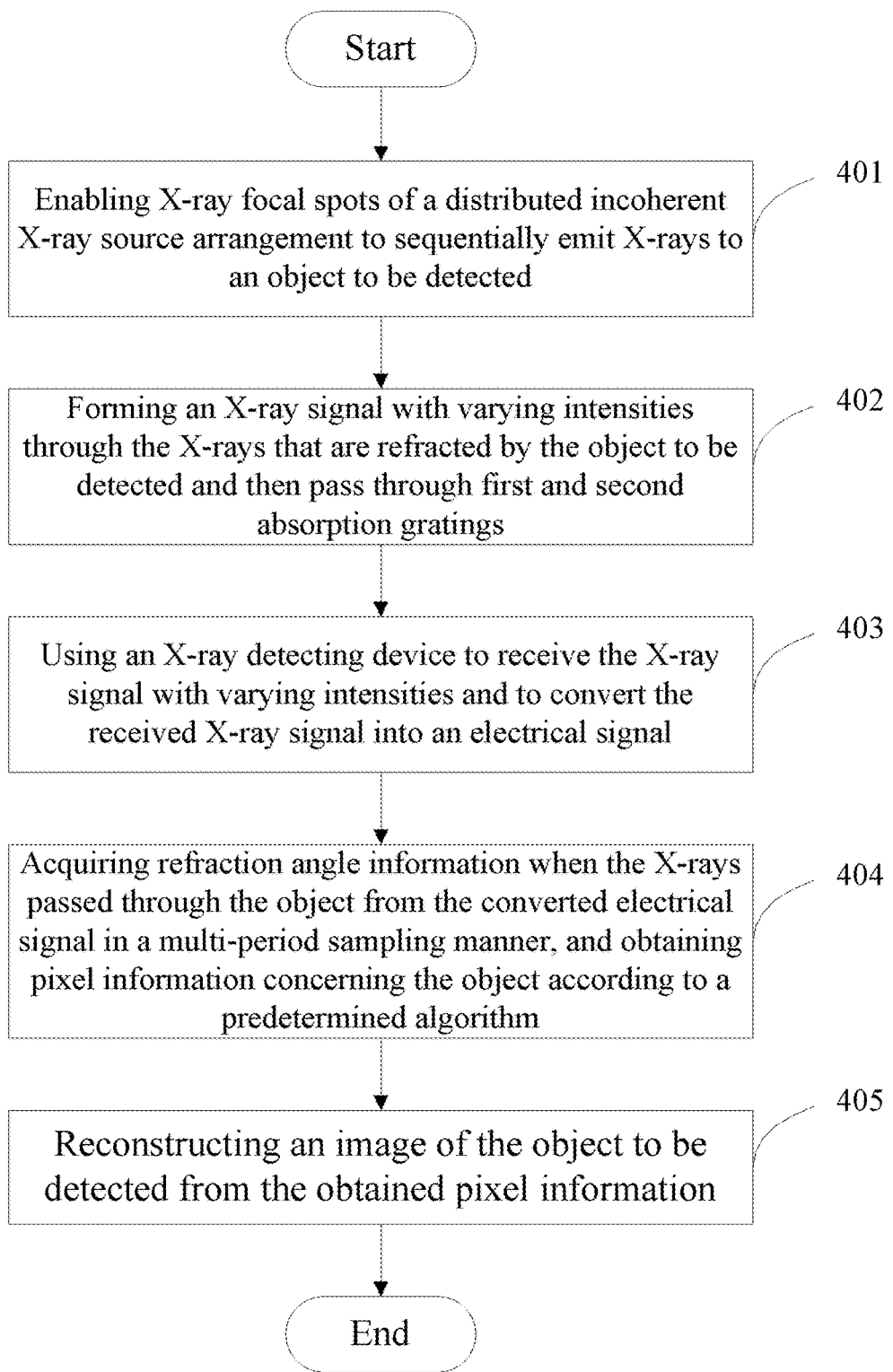
FIG. 4 is a flow chart of an imaging method by using X-rays, according to an embodiment of the disclosure.

FIG. 4 shows a flow chart of a method for imaging and detecting an object by using X-rays according to an embodiment of the disclosure. As shown in FIG. 4, the method for imaging and detecting an object by using X-rays according to an embodiment of the present disclosure comprises the following steps: at Step 401, X-ray focal spots of a distributed incoherent X-ray source arrangement sequentially emit X-rays to an object to be detected. At Step 402, each time the distributed incoherent X-ray source arrangement emits X-rays, the X-ray are refracted by the object to be detected and then pass through a first absorption grating and a second absorption grating (i.e., the grating G1 and the grating G2), thereby forming an X-ray signal with varying intensities. At Step 403, an X-ray detecting device receives the X-ray signal with varying intensities and converts it into an electrical signal. At Step 404, refraction angle information when the X-rays passed through the object is acquired from the converted electrical signal in a multi-period sampling manner, and pixel information concerning the object (for example, pixel value) is obtained according a predetermined algorithm. Furthermore, at Step 405, an image of the object to be detected is reconstructed from the obtained pixel information. Moreover, as described above, attenuation information and scattering information can be obtained from the received X-rays with varying intensities. Therefore, the present disclosure can simultaneously acquire attenuation information, attenuation information and scattering information, and thus can simultaneously obtain phase-contrast image, dark-field image and attenuation image of an object to be detected.

The present disclosure can be applied to an X-ray grating-based CT phase-contrast imaging system. According to an embodiment of the present disclosure, the X-ray grating-based CT phase-contrast imaging system comprises, in addition to the aforementioned structures, a rotating device. The rotating device is adapted to relatively rotate the object to be detected with respect to the X-ray source, gratings, detecting device (X-ray detecting device) and the like. In a CT mode, the multi-spectrum X-ray grating-based CT imaging system can rotate the object to be detected to obtain refraction angle information and corresponding planar pixel information at various projection angles, and then reconstruct cross-section images of the interior of the object by use of predetermined algorithms, which can show distribution of refractive index.

As described above, one of main advantages of the present disclosure is it does not rely on high-precision translation device. The present disclosure adopts a process in which a number of X-ray sources sequentially generate X-rays, instead of stepping procedure. Therefore, the present disclosure can substantially reduce imaging time and does not require high equipment accuracy of imaging system. Furthermore, as similar to the Patent Reference 1, the present disclosure does not rely on coherence of radiation source and does not have a limitation on Talbot distance. Therefore, the present disclosure can use gratings with periods in a micrometer level or larger periods and can perform incoherent phase-contrast imaging in sub-decimeter level for example at airport. Furthermore, as compared to conventional X-ray imaging techniques, the present disclosure can achieve high contrast imaging of weak-absorbing substances (for example, mammary gland, soft tissues such as blood vessel and muscle, fiber material, insects and the like). Furthermore, as compared to existing phase-contrast imaging techniques, the present disclosure can lower difficulty in manufacture of gratings that have periods in micrometer level and a large depth-to-width ratio. The present disclosure can be conveniently applied in phase-contrast imaging using high energy X-rays (for example, the energy is larger than 40 keV). The present disclosure develops novel concepts and approaches for applying the phase-contrast imaging technique into various fields such as medical, biology and industrial materials, and has great practical significance and application value.

Application Examples

Below, several application examples of the present disclosure will be described.

Figure 5:
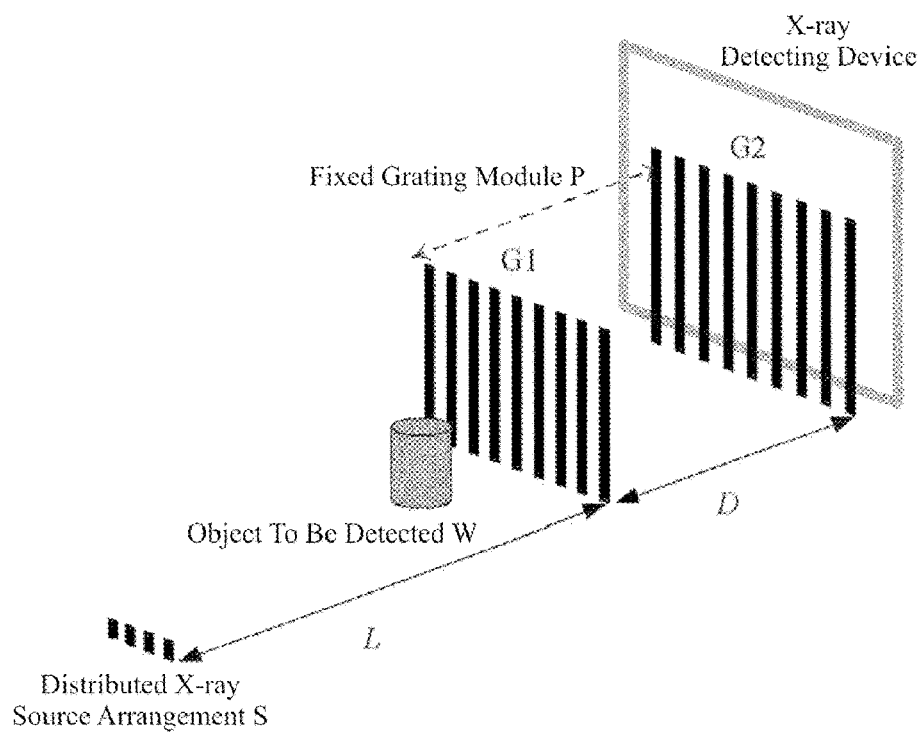
FIG. 5 is a schematic diagram of an application example of the disclosure.

FIG. 5 is a schematic diagram of a first application example of the disclosure. As shown in FIG. 5, the first application example shows a case where the X-ray phase-contrast imaging system based on the distributed X-ray source arrangement according to the embodiment of the present disclosure is applied into X-ray photography. The X-ray grating-based imaging system can simultaneously acquire three kinds of images (i.e., attenuation, phase-contrast and dark-field) during one scanning process, and thus can be applied into new-generation mammary machine and the like.

Figure 6:
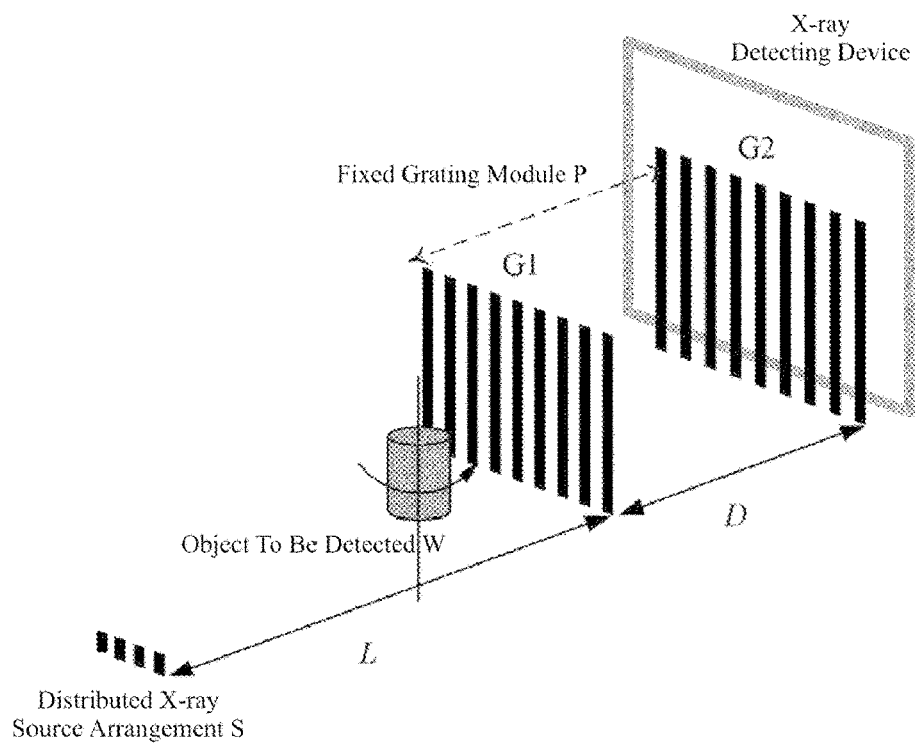
FIG. 6 is a schematic diagram of another application example of the disclosure.

Furthermore, FIG. 6 is a schematic diagram of a second application example of the disclosure. As shown in FIG. 6, the second application example shows a case where the X-ray phase-contrast imaging system based on the distributed X-ray source arrangement according to the embodiment of the present disclosure is applied into X-ray CT imaging. The sample to be scanned W can be rotated around a direction perpendicular to a path of X-ray beam. Therefore, three-dimensional information concerning substance structure can be obtained.

Figure 7:
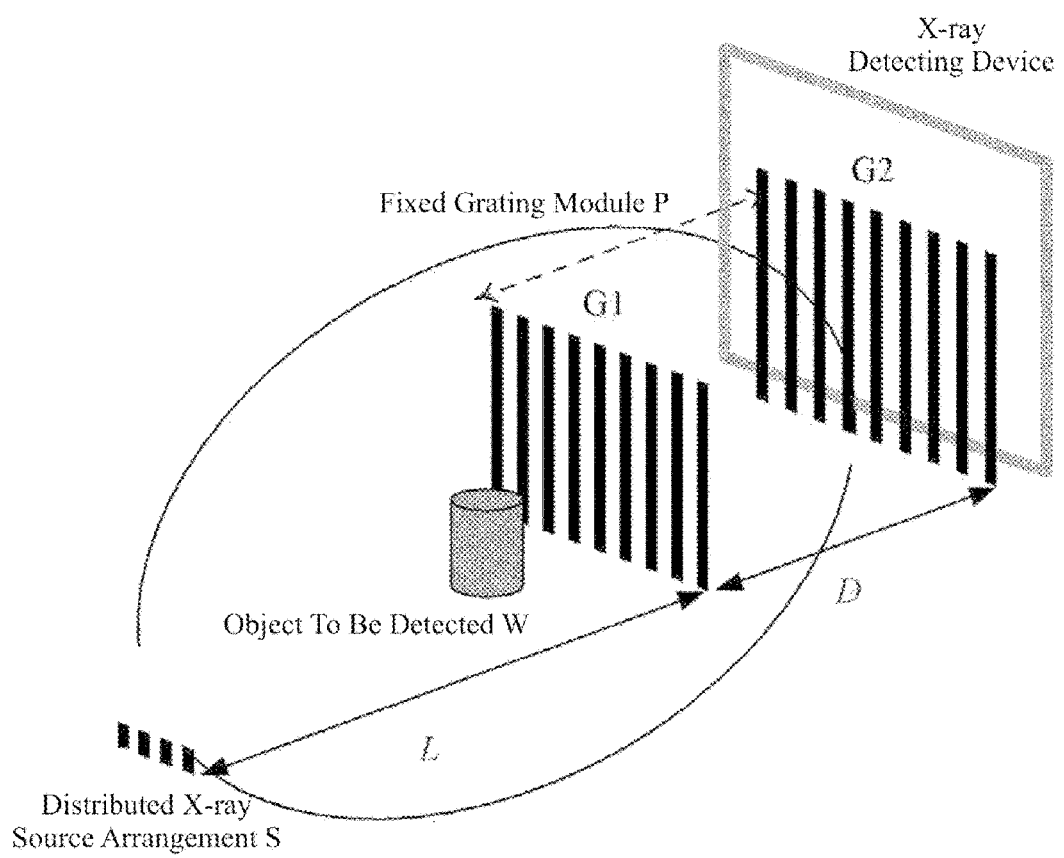
FIG. 7 is a schematic diagram of another application example of the disclosure.

Furthermore, FIG. 7 is a schematic diagram of a third application example of the disclosure. As shown in FIG. 7, the third application example shows a case where the X-ray phase-contrast imaging system based on the distributed X-ray source arrangement according to the embodiment of the present disclosure is applied into X-ray CT imaging. The mechanical structure of the entire multi-spectrum X-ray grating-based imaging system can be rotated around a direction perpendicular to a path of X-ray beam. Therefore, three-dimensional information concerning substance structure can be obtained.

As stated above, the X-ray phase-contrast imaging system based on the distributed X-ray source arrangement according to the disclosure adopts a distributed incoherent X-ray source arrangement instead of conventional X-ray sources, wherein a conventional stepping procedure which translates gratings via mechanical devices is replace with a process in which a number of distributed X-ray sources sequentially generate X-rays (stepping exposure procedure). Therefore, the imaging system according to the present disclosure can reduce scanning time and does not require high accuracy translation. The imaging system according to the present disclosure does not have high standards with respect to vibration reduction and environment temperature, and thus can facilitate application of grating-based imaging systems.

The present disclosure innovatively combines distributed X-ray source technique with grating-based imaging technique. The present disclosure gives full play to superiorities of grating-based imaging technique. For example, three kinds of information (i.e., attenuation, phase-contrast and dark-field) that indicate internal structure of object may be simultaneously obtained during one scanning process such that internal structural information and composition information of object can be more fully revealed. Furthermore, the present disclosure adopts a distributed X-ray source arrangement that can generate plural exposures with short intervals and adopts stepping exposure procedure instead of mechanical stepping procedure. Therefore, the present disclosure can perform quick and stable imaging via grating-based imaging technique, and thus can be widely used in various fields such as medical imaging, security checking and the like.

It should be understood that the disclosure is not limited to the precise structure as described above and shown in the figures, but can have various modification and alternations without departing from the scope of the disclosure.

What is claimed is:

1. An X-ray phase-contrast imaging system, comprising:
a distributed incoherent X-ray source arrangement;
a fixed grating module, comprising a first grating and a second grating which are disposed in parallel to each other and are fixed relative to each other; and
an X-ray detecting device.

2. The X-ray phase-contrast imaging system according to claim 1, wherein
X-ray sources of the distributed incoherent X-ray source arrangement are arranged in a direction perpendicular to both an X-ray propagation direction and a grating strip direction.

3. The X-ray phase-contrast imaging system according to claim 2, wherein
the X-ray phase-contrast imaging system further comprises a computer workstation, which is configured to control the distributed incoherent X-ray source arrangement and the X-ray detecting device such that:
the X-ray sources of the distributed incoherent X-ray source arrangement sequentially generate X-rays to emit X-rays to an object to be detected;
for each exposure, the X-ray detecting device receives the X-rays, wherein after a series of stepping exposures of the distributed incoherent X-ray source arrangement and corresponding data acquisitions, at each pixel of the X-ray detecting device, X-ray intensities are represented as an intensity curve;

the intensity curve at each pixel spot on the X-ray detecting device is compared to an intensity curve in the absence of the object to be detected, and a pixel value at each pixel is obtained from a variation of the intensity curves; and an image of the object to be detected is reconstructed from the obtained pixel values.

4. The X-ray phase-contrast imaging system according to claim 3, further comprising: an actuation device for, under the control of computer workstation, enabling the object to be detected to rotate by an angle relative to other parts of the X-ray imaging system.

5. The X-ray phase-contrast imaging system according to claim 4, wherein at each rotation angle, the phase stepping and exposure actions are repeated, and then an image of the object to be detected is reconstructed according to a predetermined CT image reconstruction algorithm.

6. The X-ray phase-contrast imaging system according to claim 3, wherein the computer workstation comprises: a data processing module, for processing data information and calculating pixel values at respective spots on the object to be detected; an image reconstruction module, for reconstructing an image of the object to be detected based on the calculated pixel values; and a control module, for controlling the distributed X-ray source arrangement and the X-ray detecting device.

7. The X-ray phase-contrast imaging system according to claim 3, wherein the computer workstation comprises: a display unit for displaying the image of the object to be detected.

8. The X-ray phase-contrast imaging system according to claim 3, wherein the computer workstation is configured to calculate refraction information of X-rays at a predetermined spot on the object to be detected by comparing the intensity curve with the presence of the object to be detected to the intensity curve in the absence of the object to be detected, and thus calculate corresponding pixel value.

9. The X-ray phase-contrast imaging system according to claim 3, wherein the computer workstation is configured to calculate scattering information of X-rays at a predetermined spot on the object to be detected by comparing the intensity curve with the presence of the object to be detected to the intensity curve in the absence of the object to be detected, and thus calculate corresponding pixel value.

10. The X-ray phase-contrast imaging system according to claim 3, wherein the computer workstation is configured to calculate attenuation information of X-rays at a predetermined spot on the object to be detected by comparing the intensity curve with the presence of the object to be detected to the intensity curve in the absence of the object to be detected, and thus calculate corresponding pixel value.

11. The X-ray phase-contrast imaging system according to claim 3, wherein the computer workstation is configured to calculate refraction information, scattering information and attenuation information of X-rays at a predetermined spot on the object to be detected by comparing the intensity curve with the presence of the object to be detected to the intensity curve in the absence of the object to be detected, and thus calculate corresponding pixel value.

12. The X-ray phase-contrast imaging system according to claim 1, wherein the distributed incoherent X-ray source arrangement uses carbon nanotubes as its electron sources.

13. The X-ray phase-contrast imaging system according to claim 1, wherein the periods of the first grating and second grating are between 0.1 and 30 μm.

14. An X-ray imaging method, comprising:

sequentially generating, by X-ray sources of a distributed incoherent X-ray source arrangement, X-rays to emit X-rays to an object to be detected;

each time the distributed incoherent X-ray source arrangement emits X-rays, forming an X-ray signal with varying intensities from the X-rays, which are refracted by the object to be detected and then pass through a first absorption grating and a second absorption grating;

by an X-ray detecting device, receiving the X-ray signal with varying intensities and converting the received X-ray signal into an electrical signal;

acquiring, from the converted electrical signal in a multi-period sampling manner, refraction angle information when the X-rays passed through the object, and obtaining pixel values of the object according to a predetermined algorithm; and reconstructing an image of the object to be detected from the obtained pixel values.

15. The X-ray imaging method according to claim 14, further comprising:

rotating the object to be detected, wherein at each rotation angle, the X-ray sources of the distributed incoherent X-ray source arrangement sequentially generates X-rays to emit X-rays to the object to be detected, and reconstructing an image of the object to be detected according to a predetermined CT image reconstruction algorithm.

16. The X-ray imaging method according to claim 14, wherein calculating refraction information of X-rays at a predetermined spot on the object to be detected by comparing an intensity curve with the presence of the object to be detected to a background intensity curve in the absence of the object to be detected, and thus calculating corresponding pixel value.

17. The X-ray imaging method according to claim 14, wherein calculating scattering information of X-rays at a predetermined spot on the object to be detected by comparing an intensity curve with the presence of the object to be detected to a background intensity curve in the absence of the object to be detected, and thus calculating corresponding pixel value.

18. The X-ray imaging method according to claim 14, wherein calculating attenuation information of X-rays at a predetermined spot on the object to be detected by comparing an intensity curve with the presence of the object to be detected to a background intensity curve in the absence of the object to be detected, and thus calculating corresponding pixel value.

19. The X-ray imaging method according to claim 14, wherein calculating refraction information, scattering information and attenuation information of X-rays at a predetermined spot on the object to be detected by comparing an intensity curve with the presence of the object to be detected to a background intensity curve in the absence of the object to be detected, and thus calculating corresponding pixel value.

20. An X-ray imaging method, which performs X-ray imaging of an object by using an X-ray imaging system, wherein the X-ray imaging system comprises: a distributed incoherent X-ray source arrangement, a fixed grating module, an X-ray detecting device and a computer workstation, the X-ray imaging method comprising the following steps:

sequentially generating, by X-ray sources of the distributed X-ray source arrangement, X-rays to emit X-rays to an object to be detected;

for each exposure, receiving the X-rays by the X-ray detecting device, wherein after a series of stepping exposures of the distributed X-ray source arrangement and corresponding data acquisitions, at each pixel of the X-ray detecting device, X-ray intensities are represented as an intensity curve;

comparing the intensity curve at each pixel spot on the X-ray detecting device to an intensity curve in the absence of the object to be detected, and obtaining a pixel value at each pixel from a variation of the intensity curves; and reconstructing an image of the object to be detected according to the obtained pixel values.

\* \* \* \* \*